Figure 1:
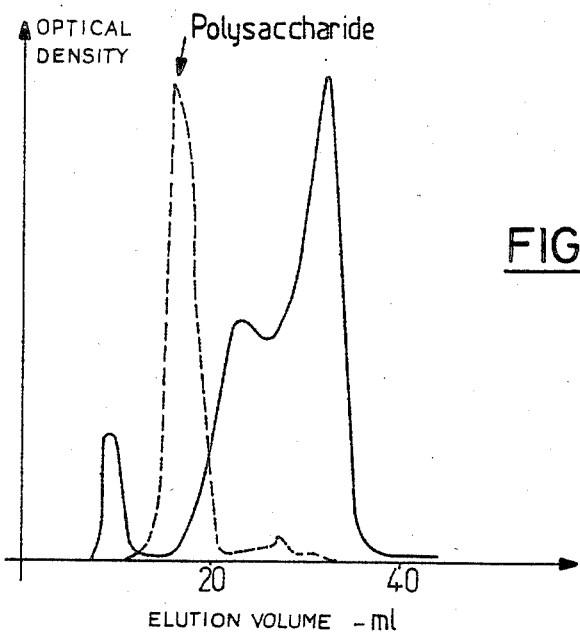

United States Patent [19]

Dussourd D'Hinterland et al.

[11] Patent Number: 4,734,403

[45] Date of Patent: Mar. 29, 1988

[54] MEMBRANE POLYSACCHARIDES WHICH ARE USEFUL AS IMMUNOSTIMULANTS

[75] Inventors: Lucien Dussourd D'Hinterland; Gérard Normier; Anne-Marie Pinel, all of Castres, France

[73] Assignee: P.F. Medicament, Paris, France

[21] Appl. No.: 770,737

[22] Filed: Aug. 29, 1985

[30] Foreign Application Priority Data

Sep. 10, 1984 [FR] France ............................ 84 13844

[51] Int. Cl.$^4$ ........................ A61K 31/71; C07H 3/00
[52] U.S. Cl. ...................................... 514/54; 536/1.1; 536/123; 435/75
[58] Field of Search ................... 536/1.1, 123; 514/54

[56] References Cited

FOREIGN PATENT DOCUMENTS 0049182  4/1982  European Pat. Off. .

OTHER PUBLICATIONS

*Chemical Abstracts,* vol. 99, 1983, No. 1932074, p. 615.

Primary Examiner—J. R. Brown
Assistant Examiner—Elli Peselev
Attorney, Agent, or Firm—Handal & Morofsky

[57] ABSTRACT

The present invention relates to a membrane polysaccharide of bacterial origin having the following quantitative analytical composition:

| | |
|---|---|
| galactose content | 66 ± 6% |
| content of hexoses other than galactose | <1% |
| hexosamine (glucosamine) content | 8.5 ± 2% |
| amino acid content | 5 ± 2% |
| fatty acid content | <1% |
| nucleic acid content | <0.005% |
| protein content | <0.03% | and molecular weight: 90,000 ± 10,000.

5 Claims, 5 Drawing Figures

MEMBRANE POLYSACCHARIDES WHICH ARE USEFUL AS IMMUNOSTIMULANTS

The present invention relates to a polysaccharide of low molecular weight (approximately 90,000) obtained from membrane proteoglycans of bacterial origin, and also a process for the preparation thereof and its use by way of a drug, especially as an immunostimulant, in particular for activating NK (natural killer) cells, and as an adjuvant in vaccines.

French Pat. No. 78/35649, filed on 19th Dec. 1978, describes a detoxified membrane proteoglycan isolated from a non-encapsulated and non-pathogenic mutant strain of *Klebsiella pneumoniae* biotype a. This proteoglycan has a molecular weight greater than 2,000,000 Daltons, and exerts characteristic adjuvant properties in respect of antibody production against antigens which are in combination with it. On the other hand, it does not possess significant NK cell-stimulatory activity. Examples are given of its use as an adjuvant in vaccine formulae.

French Pat. No. 82/03921, filed on 9th Mar. 1982, describes the production, from the above proteoglycan and through the action of lysozyme, of a proteoglycan fraction of molecular weight between 200,000 and 400,000 Daltons. This proteoglycan fraction possesses a novel property: that of very strongly stimulating NK cell activity via induction of an endogenous interferon. This fraction, on the other hand, no longer possesses the adjuvant properties of the detoxified proteoglycan described above.

The present invention relates to a novel compound originating, in particular, from bacterial membranes; it is a polysaccharide having a molecular weight between 80,000 and 100,000 Daltons and having the following composition in lyophilized form:

| | |
|---|---|
| galactose content | 66 ± 6% |
| content of hexoses other than galactose | <1% |
| hexosamine (glucosamine) content | 8.5 ± 2% |
| amino acid content | 5 ± 2% |
| fatty acid content | <1% |
| nucleic acid content | <0.005% |
| protein content | <0.3% |

Characteristic features of this novel polysaccharide obtained from soluble membrane proteoglycans of bacterial origin are its low molecular weight (90,000±10,000) and its special composition; in effect, it contains only a single hexose, galactose, and a single hexosamine, glucosamine, to which are attached peptides corresponding to the amino acids analyzed. Since, in addition, this polysaccharide is virtually free of fatty acids, nucleic acids and proteins, this is a well-defined product, the structure of which has, moreover, been able to be determined.

Study of the structure of the polysaccharide by means of classical methods such as periodic oxidation, methylation, gas chromatography coupled to mass spectrometry, NMR, and the like, has enabled the sequence of linkage of its constituents to be defined precisely.

The results obtained show that this polysaccharide consists of the repeated linking of monomeric units having the following structure:

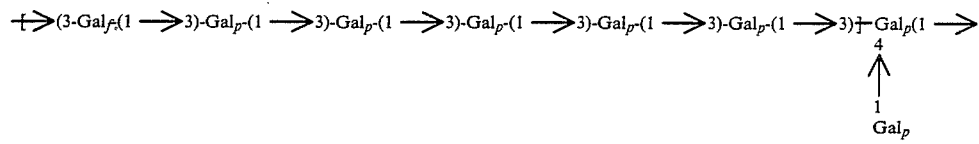

where
Gal$_f$ = galactofuranose,
Gal$_p$ = galactopyranose (in $\alpha$ and $\beta$ forms), which corresponds to the following structural formula:

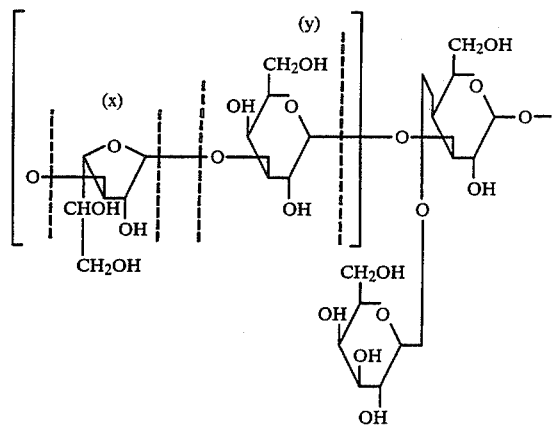

where x=1 and y=6.

This polysaccharide can be prepared by different processes.

In the preferred process, according to the present invention, for preparing the membrane polysaccharide of bacterial origin:

(a) starting with a strain of a gram-negative bacterium, the water-soluble proteoglycans are extracted from the membranes;

(b) from the said soluble proteoglycans, polysaccharides of molecular weight between 80,000 and 100,000 are isolated; and (c) if necessary, the isolated polysaccharides are purified by removing the proteins present in the fraction isolated.

Among the gram-negative bacteria capable of being employed, *Klebsiella pneumoniae*, *Serratia marcescens* and *Escherichia coli* may be mentioned; especially *Klebsiella pneumoniae*, which forms the subject of a filing in the Collection Nationale de Culture de Microorganismes (CNCM) (National Collection of Microorganism Cultures) under No. 145-I-IP.

The soluble proteoglycans are preferably prepared by solubilization of crude membrane proteoglycans obtained carrying out processes described in the prior art, especially by the processes described in French Pat. No. 78/35649. This is, essentially, the process in which the membranes are separated from a ground cell preparation by several centrifugations.

The crude proteoglycans obtained are treated with a base, especially an alkali metal hydroxide, preferably sodium hydroxide, at a molarity of between 0.3 and 1M, preferably 0.5M, the treatment being continued for several hours, for example 1 hour, at a temperature between 50° and 60° C., for example 56° C., preferably with agitation.

Compared to the process described in French Pat. No. 78/35649, the medium used is more basic to ensure more complete hydrolysis of the crude proteoglycans.

To remove the excess reagent, after cooling, the suspension is neutralized with an acid, for example hydrochloric acid, and then clarified by removing the insoluble residue by sedimentation, especially by centrifugation, for example for 60 minutes at 30,000 g.

The supernatant, which constitutes the soluble proteoglycans, is collected and can be lyophilized.

The membrane polysaccharide of bacterial origin having the desired molecular weight is then isolated from the supernatant by a fractionation process, preferably a chromatographic fractionation. The column elution fraction containing the polysaccharide of molecular weight between 80,000 and 100,000 is collected.

This chromatographic fractionation can be performed using an agarose resin such as Sepharose CL-2B, but other fractionation techniques can be employed.

The polysaccharide can then be purified, in one embodiment of the invention, especially by removing the proteins of molecular weight close to that of the isolated polysaccharide, for example by enzymic hydrolysis of the said proteins, especially by the action of proteinase, followed by a separation of purified polysaccharides by a fractionation process, preferably a chromatographic fractionation.

The fraction containing the polysaccharide can then be collected and optionally lyophilized. The lyophilizate thereby obtained constitutes the polysaccharide which forms the subject of the present invention.

The present invention also relates to the use of these proteoglycans by way of a drug, either alone or in combination with a vaccinating agent.

In effect, the polysaccharide according to the invention possesses immunostimulatory properties, of which the main properties are:

an adjuvant power, especially at very low doses, for vaccines, especially ribosomal vaccines;

a high capacity for stimulating NK cells, in vitro and in vivo.

Thus, a strong activation of the NK cells has been demonstrated for these products in vivo in mice towards Moloney's lymphoma (YAC-1 cell).

Furthermore, adjuvant properties have been demonstrated towards vaccines, especially ribosomal vaccines, that is to say vaccines in which the vaccinating agent consists of ribosomes, but other vaccinating agents can be used.

Taking into account the activities demonstrated, it is clear that the nature of the pharmaceutical compositions as well as the dosages to be employed, may vary within a very wide range. In effect, the activation of the NK cells may depend to a great extent on the target cells aimed at, and the state of the patient. Likewise, in the case of the adjuvants, only an optimization study may enable the ratio to be established between the adjuvant and the vaccinating agent, as well as the dosages.

The examples below will enable further characteristics and advantages of the present invention to be demonstrated.

Figure 2:
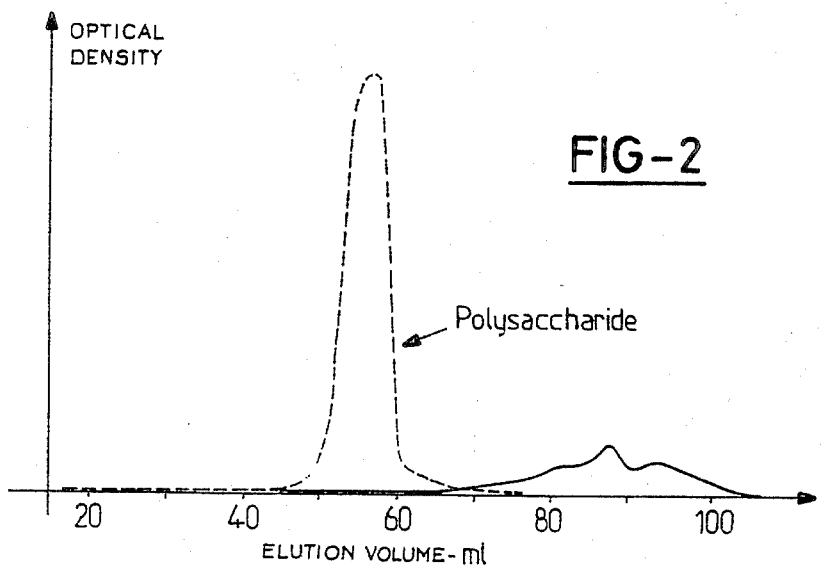
Figure 3:
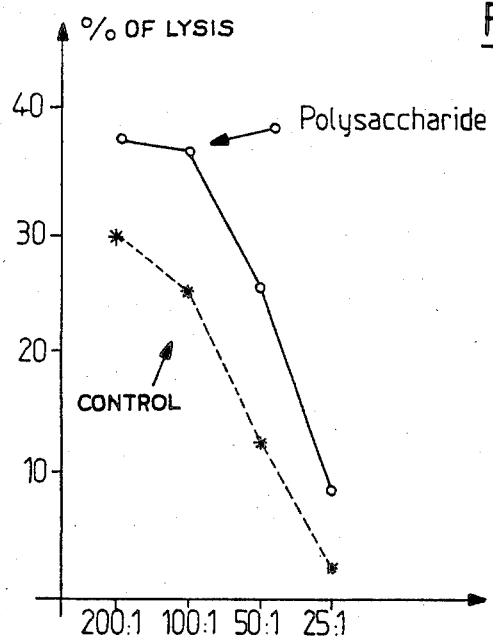
Figure 4:
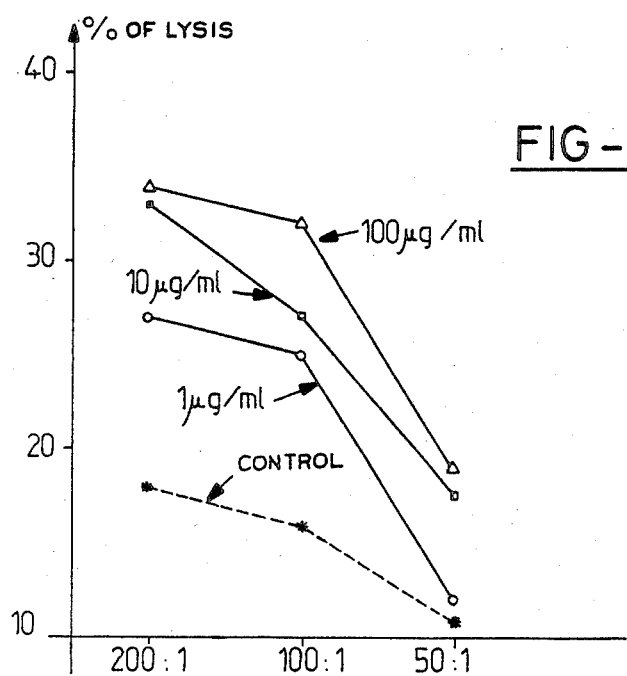
Figure 5:
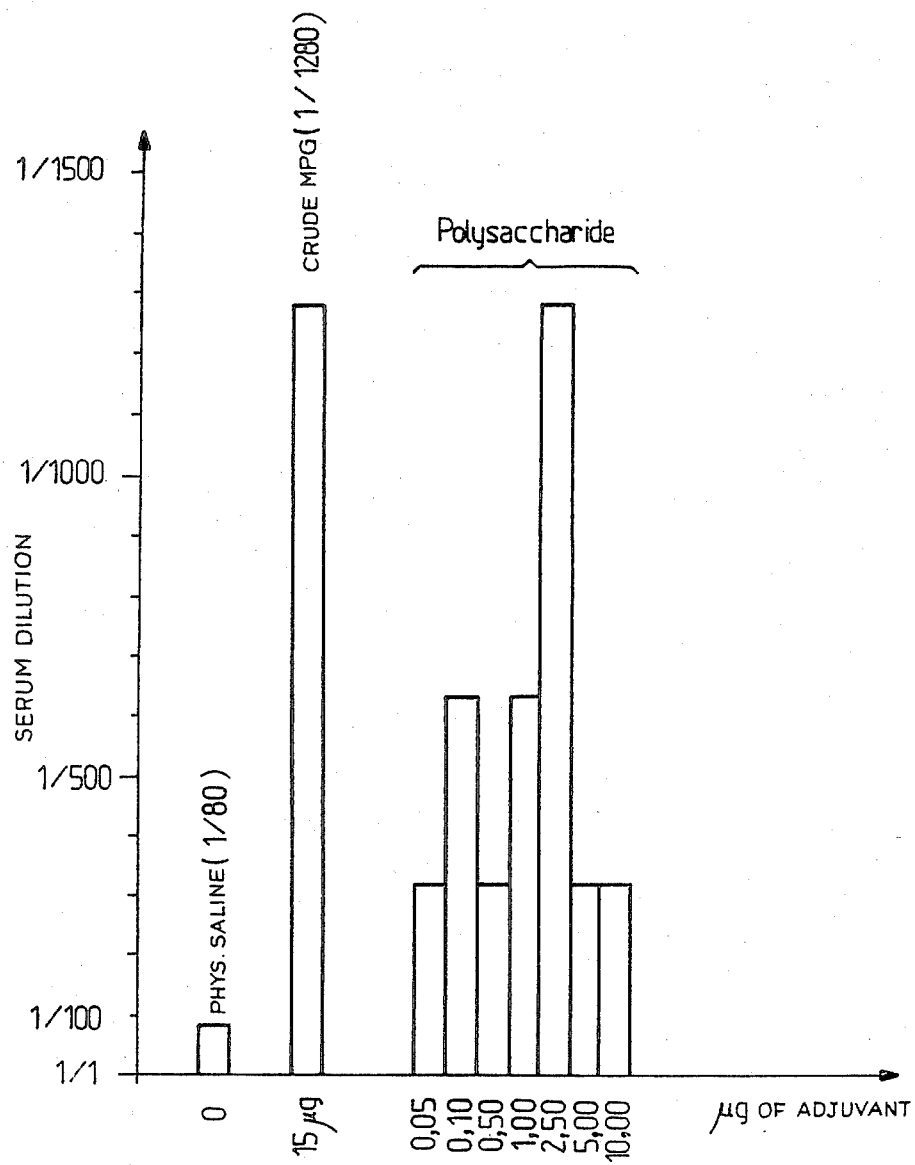

The attached figures illustrate some particular aspects of the invention. In these figures:

FIG. 1 is a chromatographic curve on Sepharose CL-28 of the proteoglycan hydrolyzed with 0.5N NaOH, FIG. 2 is a chromatographic curve on Sephacryl S-200 of the polysaccharide treated with proteinase, FIG. 3 shows the curves for NK cell activation in vitro (Example 6), FIG. 4 shows the curves for NK cell activation in vivo (Example 7), FIG. 5 shows a histogram of the ELISA assay obtained in Example 8.

EXAMPLE 1

Isolation of the crude membrane proteoglycans

The biomass of the *Klebsiella pneumoniae* strain 145-I-IP is dispersed in ice-cold 0.01M Tris HCl buffer, pH 7, containing 0.15M NaCl, and then subjected to mechanical grinding designed to break the cell walls.

The bacterial lysate is clarified by centrifugation for 10 minutes at 7,500 g, and the supernatant is then centrifuged for 60 minutes at 30,000 g.

The pellet is dispersed in 0.15M aqueous NaCl solution. The suspension obtained is again clarified for 10 minutes at 7,500 g and then centrifuged for 45 minutes at 30,000 g.

The pellet is taken up in distilled water and again subjected to a cycle of centrifugation at 7,500 g and then at 30,000 g.

The pellet of crude membrane proteoglycans is then taken up in ¼ the initial volume of sterile distilled water, the suspension is clarified for 10 minutes at 7,500 g and the supernatant is lyophilized.

EXAMPLE 2

Preparation of soluble membrane proteoglycans

The lyophilized crude membrane proteoglycans are dispersed in NaOH (0.5M) and then hydrolyzed for 1 hour at 56° C. After being cooled, the suspension is neutralized with HCl. The suspension is then clarified by centrifugation for 60 minutes at 30,000 g and the supernatant is then collected. The filtrate is lyophilized.

EXAMPLE 3

Isolation of the polysaccharide by chromatographic fractionation

The above lyophilisate is dissolved in 0.01M Tris HCl buffer, pH 7, and then subjected to a first chromatographic fractionation on a column (60×2.6 cm) of Sepharose CL-2B (Pharmacia, Sweden) (agarose gel of specified porosity) equilibrated in the same buffer.

FIG. 1 gives an example of chromatographic separation obtained at this stage, with an indication of the precise localization of the polysaccharide peak shown as a broken line.

On this chromatogram, it is noted that the polysaccharide peak is completely separated from a peak of very much higher molecular weight eluted first from the column, and incompletely separated from a combination of protein fractions having a lower molecular weight close to that of the polysaccharide, eluted after the latter.

The elution fraction containing the polysaccharide is collected, dialyzed against distilled water and then lyophilized.

This fraction is still slightly contaminated with proteins of molecular weight very close to that of the polysaccharide (70,000 to 100,000). These proteins will hence be hydrolyzed by the action of an enzyme before the final stage of chromatographic fractionation.

EXAMPLE 4

Enzymic hydrolysis of the residual proteins

The above lyophilisate is dissolved in 0.01M Tris HCl buffer, pH 7.3, containing 1.1 mM EDTA, in the proportion of 20 mg/ml. 50 mg/ml of proteinase K (proteolytic enzyme of Tritirachium album) are then added to this solution, which is then incubated for 2 hours at 37° C. with agitation.

EXAMPLE 5

Purification of the polysaccharides by chromatographic fractionation

The contaminating proteins, the molecular weight of which has been reduced by proteolysis, are separated from the polysaccharide by chromatography on Sephacryl S-200 (Pharmacia, Sweden) (polyacrylamide gel of defined porosity).

FIG. 2 gives an example of the chromatographic separation obtained at this stage.

On this chromatogram, it is noted that the polysaccharide peak shown by the broken line is now completely separated from that of the hydrolyzed proteins shown by the continuous line, the elution of which from the column is thus strongly retarded relative to the polysaccharide.

The fraction containing the pure polysaccharide is then collected, concentrated and dialyzed continuously against distilled water over a membrane having a cutoff threshold at 10,000 Daltons, sterilized by filtration on a 0.2-$\mu$ membrane and then lyophilized.

The lyophilisate thereby obtained constitutes the polysaccharide of Klebsiella pneumoniae which forms the subject of the present patent.

EXAMPLE 6

Activation of NK cells in vitro

Procedure $10^7$ normal mouse spleen cells per ml of RPMI 1640 medium with 5% of fetal calf serum added.

Incubation at 37° C. in a $CO_2$ incubator with variable amounts of polysaccharide.

The target cells are $^{51}Cr$-labeled YAC-1 cells (Moloney's lymphoma) sensitive to NK cells.

The measurement of lysis is carried out by counting the $^{51}Cr$ released for effector cell/target cell ratios of 200:1, 100:1 and 50:1 during a 4 hours' incubation.

Results

These are extremely clear, and demonstrate a highly significant increase in the percentage of target cells lysed ($P<0.01$) from a dose of 1 $\mu$g/ml upwards.

FIG. 3 gives an example of the results obtained in this study.

EXAMPLE 7

Intraperitoneal activation of NK cells in vivo in mice

Procedure

Animals: CBA/J mice aged from 4 to 5 months.

Target cells: YAC-1 (Moloney's lymphoma) sensitive to NK cells.

The polysaccharide is injected intraperitoneally at a dose of 50 $\mu$g in 0.2 ml of buffered physiological saline 3 days before measuring the NK activity. Control mice only receive physiological saline under the same conditions.

The spleen cells are then removed and incubated as above with $^{51}Cr$-labeled target cells in effector cell/target cell ratios of 200:1, 100:1, 50:1, and 25:1 for 4 hours. The $^{51}Cr$ released is measured to determine the percentage of target cells lysed.

Results

A highly significant increase in the NK activity is observed in the animals treated with the polysaccharide, in comparison with the control animals.

FIG. 4 gives an example of the results obtained in this study.

EXAMPLE 8

Adjuvant properties of the polysaccharide

Example of study of the adjuvant properties of the polysaccharide as regards a Streptococcus pyogenes group A ribosomal antigen.

Principle

Mice are immunized with a constant dose of Streptococcus pyogenes ribosomes to which variable doses of polysaccharide are added. The specific antibody response against the ribosomes is then measured by the ELISA technique.

Control groups are treated, one with physiological saline, and the other with the standard dose of Klebsiella pneumoniae crude membrane proteoglycan (crude MPG).

Procedure 9 batches of 10 female NMRI mice aged 8 weeks. Each animal receives 5 injections in 15 days.

batch 1: physiological saline
batch 2: 10 $\mu$g of ribosomes + 0.05 $\mu$g of polysaccharide
batch 3: 10 $\mu$g of ribosomes + 0.1 $\mu$g of polysaccharide
batch 4: 10 $\mu$g of ribosomes + 0.5 $\mu$g of polysaccharide
batch 5: 10 $\mu$g of ribosomes + 1.0 $\mu$g of polysaccharide
batch 6: 10 $\mu$g of ribosomes + 2.5 $\mu$g of polysaccharide
batch 7: 10 $\mu$g of ribosomes + 5.0 $\mu$g of polysaccharide
batch 8: 10 $\mu$g of ribosomes + 10.0 $\mu$g of polysaccharide
batch 9: 10 $\mu$g of ribosomes + 15.0 $\mu$g of crude MPG.

The animals are bled on the 21st day and the titers of antibodies to Streptococcus pyogenes ribosomes are determined by the ELISA technique.

The results indicate the final dilution of the serum giving a positive response in ELISA, and are shown in the form of a histogram below.

Results

FIG. 5 is a representation in the form of a histogram of the ELISA assay of the specific antibody response as a function of the dose of polysaccharide combined with the antigen.

Antigen: 10 $\mu$g of S. pyogenes ribosomes per injection.

These results show that a 2.5 $\mu$g dose of polysaccharide has the same adjuvant effect as a 15 $\mu$g dose of crude MPG, equivalent to a specific activity 6-fold greater under these conditions.

We claim:

1. Membrane polysaccharide of bacterial origin useful as a immunostiulant and having the following quantitative analytical composition:

| | |
|---|---|
| galactose content | 66 ± 6% |
| content of hexoses other than galactose | <1% |
| hexosamine (glucosamine) content | 8.5 ± 2% |
| amino acid content | 5 ± 2% |

| | |
|---|---|
| fatty acid content | <1% |
| nucleic acid content | <0.005% |
| protein content | <0.3% |
| and molecular weight: 90,000 ± 10,000. | |

2. Polysaccharide of molecular weight of about 60,000±10,000 daltons and having a polymeric structure comprising of about 40±7 repeating units of the monomer:

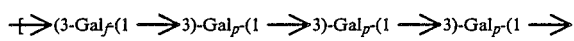

where
Gal$_f$ = galactofuranose
Gal$_p$ = galactopyranose (in $\alpha$ and $\beta$ form).

3. Polysaccharide as claimed in claim 2, in which the monomer is represented by the structural formula:

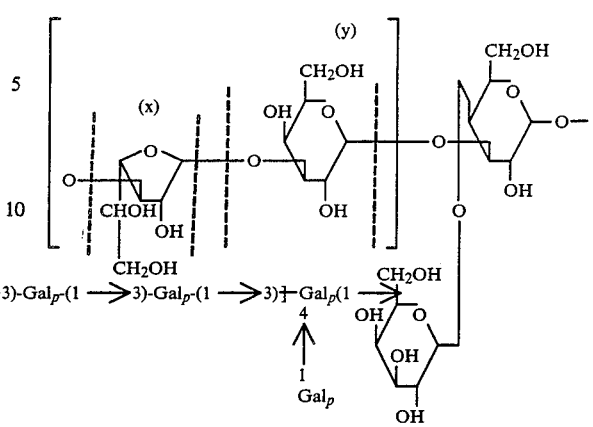

where x=1; y=6.

4. Pharmaceutical composition useful as an immunostimulant comprising an effective amount of the polysaccharide of claim 1, together with pharmaceutically acceptable carrier.

5. The composition of claim 4, which further contains a vaccinating agent.

* * * * *